US00PP33694P2

(12) United States Plant Patent
Hansen

(10) Patent No.: US PP33,694 P2
(45) Date of Patent: Nov. 23, 2021

(54) ***HEUCHERA* PLANT NAMED 'TOFFEE TART'**

(50) Latin Name: ***Heuchera* hybrid**
Varietal Denomination: Toffee Tart

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,293

(22) Filed: Dec. 18, 2020

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./440, 250, 263.1
CPC ... A01H 5/02; A01H 5/12; A01H 5/00; A01H 6/80; A01H 6/12
See application file for complete search history.

(56) References Cited

U.S. PATENT DOCUMENTS

PP18,386 P2 * 1/2008 Delabroye ..... A01H 5/12 Plt./440

OTHER PUBLICATIONS

Digger Magazine Farwest New Varieties Showcase 2020, retrieved on Apr. 7, 2020, retrieved from the Internet at http://www.diggermagazine.com/wp-content/uploads/2020/08/New-Varieties-2020-Final.pdf, 34-48. (Year: 2020).*

* cited by examiner

*Primary Examiner* — June Hwu

(57) ABSTRACT

The new and distinct hybrid of *Heuchera* plant named 'Toffee Tart' with rounded, shallowly-dissected leaf blades of amber color develop a light silvery overlay between the veins in spring developing a ginger coloration with silvery overlay between the veins later in the season. The new plant has reddish-brown calyces on short, upright, branched panicles producing creamy white flowers. The new plant is vigorous and produces medium clumps with many dense leaves and is useful in the landscape or in containers.

2 Drawing Sheets

Botanical denomination: *Heuchera* hybrid.
Variety denomination: 'Toffee Tart'.

STATEMENT REGARDING PRIOR DISCLOSURES UNDER 37 CFR 1.77(b)(6)

The introduction of *Heuchera* 'Toffee Tart' was in a non-enabling brief description and photograph on a website maintained by Walters Gardens, Inc. on Dec. 1, 2019. It was first privately sold on Mar. 3, 2020 by Walters Gardens, Inc. to Four Star Greenhouse, Inc. Subsequently, on May 20, 2020, Walters Gardens, Inc. introduced the new plant in the "Walters Gardens 2020-2021 Catalog." Walters Gardens, Inc. obtained the new plant and information about the new plant directly from the inventor. No plants of *Heuchera* 'Toffee Tart' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Toffee Tart'. *Heuchera* 'Toffee Tart' was hybridized by the inventor on Feb. 23, 2016 in the greenhouses of a wholesale perennial nursery in Zeeland, Mich., USA and assigned the breeder code 16-10-1. The seed or female parent was the proprietary, unreleased and unnamed hybrid assigned the breeder code K11-73-1 (not patented) and the male parent was the proprietary unreleased and unnamed hybrid assigned the breeder code 15-113-1 (not patented).

*Heuchera* 'Toffee Tart' was first selected in the fall of 2016 and passed final evaluation in the fall of 2018 from among thousands of other seedlings from the same cross and hundreds of other crosses. *Heuchera* 'Toffee Tart' has been asexually propagated by basal shoot cuttings at the same nursery in Zeeland, Mich. in 2017 and by careful shoot tip tissue culture propagation, and the resultant plants have remained stable and continued to exhibit the same characteristics as the original plant for multiple generations.

BRIEF SUMMARY OF THE INVENTION

The following traits distinguish *Heuchera* 'Toffee Tart' as a distinct hybrid plant. In comparison to the female parent and the cultivars hybridized to produce the female parent, *Heuchera* 'Toffee Tart' has more flatter, more silver leaves with less purple undertones in mid-season, with deep red calyces on upright, medium-density, compound-branched stems. The most similar cultivars known to the inventor are 'Caramel' U.S. Plant Pat. No. 16,560 and 'Ginger Ale' U.S. Plant Pat. No. 18,173 and 'Ginger Peach' U.S. Plant Pat. No. 22,257. 'Toffee Tart' has larger and flatter foliage with shallower incisions between the lobes than all of these comparison cultivars. 'Caramel' has foliage that is more amber-apricot colored, and the older foliage does not develop the silvery variegation between the veins. 'Ginger Ale' has smaller leaves that tend to have less reddish coloring and more yellow. 'Ginger Peach' has more ruffled leaf margins and the color tends to be more coppery-rose.

Plants or photography of the female and male parents were not maintained, so no further comparison is possible.

*Heuchera* 'Toffee Tart' differs from its parents as well as all other coral bells known to the applicant in the following combined traits:

1. The medium-sized, rounded, leaf blades are shallowly dissected and mostly flat.
2. Leaves are amber and before flowering develop a light silvery overlay between the veins in the spring.
3. Leaves become a ginger color with a light silvery overlay between the veins as they mature.
4. Produces medium-sized clumps and many individual leaves.
5. Plant habit is vigorous and compact with short flowering stems of creamy white flowers.

BRIEF DESCRIPTION OF THE DRAWINGS

The photographs of the new plant demonstrate the overall appearance of *Heuchera* 'Toffee Tart' including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
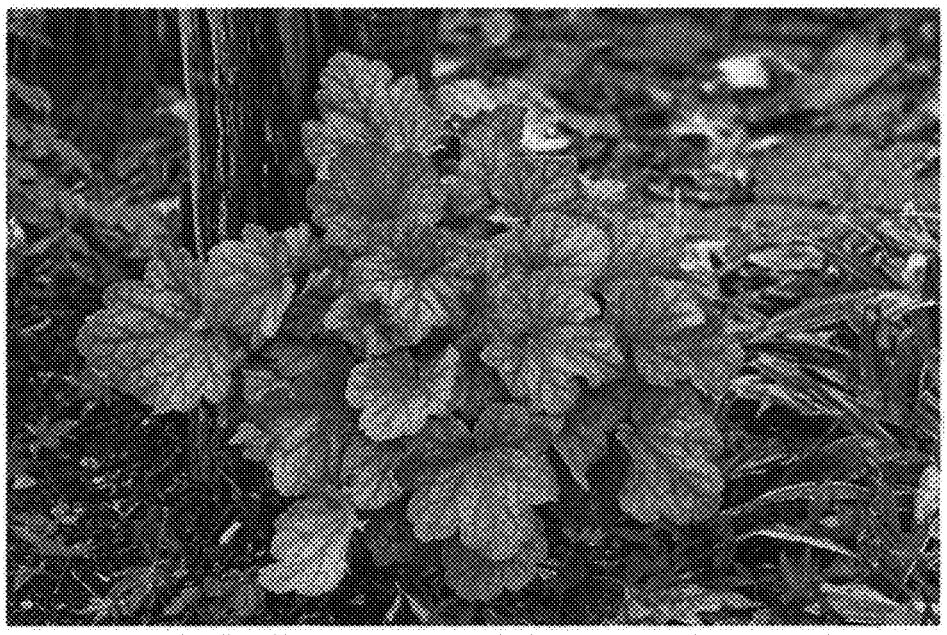
FIG. 1 shows a two-year-old plant late in the season.
Figure 2:
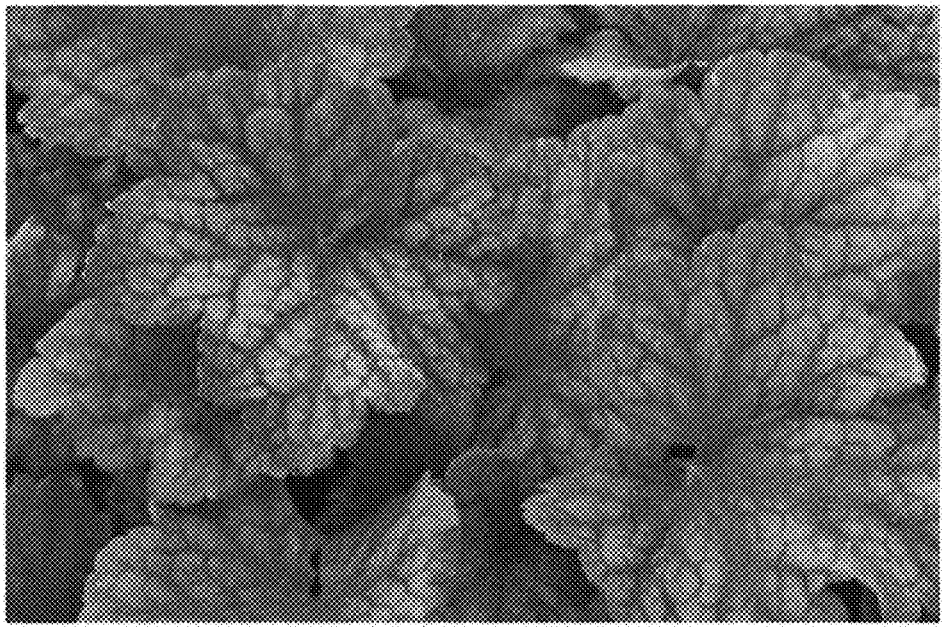
FIG. 2 shows a close-up of the foliage.
Figure 3:
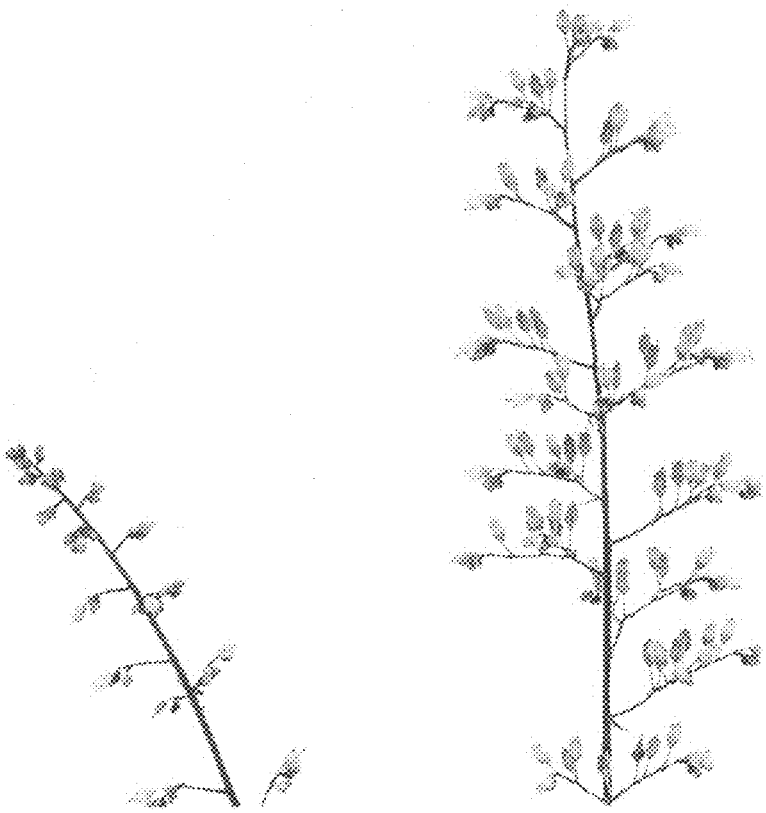
FIG. 3 shows a close-up of the flowers.

The following description is based on a two-year-old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'K11-73-1 (comprising 'Southern Comfort' U.S. Plant Pat. No. 20,364, a select unnamed form of *H. parishii* (not patented)), and the male or pollen parent was 15-113-1 (comprising 'Dark Mystery' (not patented), 'Fire Chief' U.S. Plant Pat. No. 21,880, 'Paprika' U.S. Plant Pat. No. 24,575, 'Ruby Bells' (not patented), 'Miracle' U.S. Plant Pat. No. 20,274, 'Autumn Leaves' U.S. Plant Pat. No. 22,103 and 'Mocha' U.S. Plant Pat. No. 18,386;

Plant habit: Hardy herbaceous perennial with basal rosette of foliage; mounded foliage about 22 cm tall and 38 cm in diameter with scapes to about 38 cm tall; stems to about 2.7 cm long and 1.2 cm diameter at base completely covered with petiole stipules, with about 20 leaves per stem and 5 main stems per plant;

Roots: Fibrous, finely branched; nearest RHS NN155B depending on soil type;

Growth rate: Vigorous, rapid; rooting from cutting in two weeks and finishing in three-liter container in about 3 months;

Foliage: Rounded; shallowly penta-lobed (dissected about 10 mm), with basal lobes frequently imbricate; mostly flat; apex and lobe apices rounded and apiculate; base cordate, margin crenate and micro-ciliolate; adaxial and abaxial surfaces sparsely micro-puberulent, adaxial matte, abaxial moderately lustrous; medium number of leaf indentations; leaf margin undulation absent to weak;

Leaf blade size: To about 13.0 cm wide and 13.0 cm long, average about 11.0 cm wide and 11.0 cm long;

Leaf color: Seasonally variable; initial spring adaxial with portions nearest 174C and other portions between RHS 164D and RHS 162D; initial spring abaxial nearest RHS 185C; young adaxial leaves prior to flowering between veins between RHS 153B and 146D, surrounding veins nearest RHS 176D; young abaxial leaves prior to flowering center nearest RHS 185D and near margin between RHS 185C and RHS 164B; flowering season adaxial between veins nearest RHS 161B, surrounding veins between RHS 165B and RHS 146B, margin between RHS 165B and RHS 165A; flowering season abaxial nearest RHS 185C; fall adaxial surrounding veins between RHS 148A and RHS 199B, between veins between RHS 161C and RHS 152D; fall abaxial between RHS 185C and RHS 184B; late season adaxial surrounding veins nearest RHS NN137B, between veins nearest RHS 191B; late season abaxial nearest RHS N186C;

Leaf quantity: Dense, about 20 per division and 100 per plant;

Veins: Palmate, hirsutulous abaxial and sparsely puberulent adaxial; costate abaxial and nearly flat adaxial;

Vein color: On emerging or early spring adaxial proximally nearest RHS 182B and distally between RHS 185C and RHS 164B; emerging or early spring abaxial between RHS 165A and RHS 165B; flowering season adaxial proximally nearest RHS 174C and distally between RHS 165A and RHS 165B; flowering season abaxial main veins and proximal secondary veins nearest RHS 182D and distally nearest RHS 186A; fall adaxial proximally nearest RHS 182B and distally nearest RHS 153A; fall abaxial proximal between RHS 182D and RHS 155A, distally nearest RHS 187C; late season adaxial proximally nearest RHS 148B and distally RHS NN137A; abaxial late season proximally between RHS 182D and RHS 155A, distally nearest RHS 187C;

Petiole: Terete, base amplexicaul; straight, stiff; outwardly to drooping with outer leaves and slightly upright with inner leaves; with pubescent hairs to about 2.0 mm long; to about 13.0 cm long and 4.0 mm across at base above stipule, average about 12.0 cm long and about 3.5 mm across above stipule;

Petiole color: Varying with season; young emerging leaf nearest RHS 182C; flowering season adaxial a blend of RHS 146C, RHS 148B and RHS 152D; mature and late season proximally nearest RHS N186C and proximally between RHS 195A and RHS 186C;

Stipule: At base of petiole; puberulent abaxial and glabrous adaxial; to about 15.0 mm long and about 16.0 cm wide at base and 12.0 mm wide at apex, with two distally-flared acute lobes about 5.0 mm long;

Stipule color: Adaxial nearest RHS 182C and abaxial between RHS 182C and RHS 152D;

Peduncle: Panicle; terete; stiff; puberulent; upright; to about 38.0 cm long and 4.0 mm diameter at base, average about 36.0 cm tall and about 3.5 mm diameter; about seven per plant with up to 320 flowers per panicle, average about 250;

Inflorescence: Compound-branched panicle with up to 17 branches to about 6.0 cm long and about 1.0 mm diameter at base, decreasing in size distally, average 14 branches per panicle; branches outwardly to slightly upwardly becoming more upwardly distally; flower density moderate; flowering in upper 17.0 cm and 12.0 cm wide;

Flowering longevity: Panicle effective for about three weeks;

Flower density: Moderately dense;

Peduncle color: Distally nearest RHS 165A, proximally nearest RHS177B blushed with nearest RHS 187A; branches nearest RHS 146B;

Pedicel: Terete, finely puberulent, to about 7.0 mm long and 0.5 mm diameter;

Pedicel color: Proximally nearest RHS 164D, distally nearest RHS 155A with hairs nearest RHS 187C;

Buds one day prior to opening: Oblong ellipsoidal; acute apex and attenuate base; puberulent; about 5.0 mm long and 2.0 mm diameter near middle;

Bud color one day prior to opening: Proximal portion nearest RHS N170C and distally nearest RHS 65A;

Flower: Perfect, campanulate, actinomorphic, about 8.0 mm long to exserted style and 6.0 mm in diameter at face; corolla to 7.0 mm long and 6.0 mm diameter; individual flowers lasting about 4 days on plant or as cut flower; rarely persistent;

Flower attitude: Outwardly to slightly upwardly;

Calyx: Five sepals; apex acute; about 7.0 mm long and 5.0 mm wide, base fused in proximal 4.5 mm to form hypanthium;

Sepals: Five; puberulent to glandular abaxial, glabrous adaxial; rarely persistent;

Calyx color: Adaxial and abaxial base nearest RHS 176D, RHS 195A and RHS 180D and distally nearest RHS 59B at apex; adaxial apex nearest RHS NN155A blushed with nearest RHS 70B, adaxial and abaxial distal portions nearest RHS 70B;

Petals: Five, linear, acute apex and attenuate base; margin entire, glabrous abaxial and adaxial; adnate to inner sepals in proximal 0.5 mm; about 4.0 mm long and 1.3 mm wide near apex;

Petal color: Abaxial and adaxial nearest RHS NN155D;

Androecium: Five;

*Filaments*.—Five; adnate to adaxial calyx about 1.0 mm above base; thin, glabrous; about 2.0 mm long and less than 0.2 mm diameter; color nearest RHS NN155D.

*Anthers*.—Ellipsoidal, distinct, basifixed, longitudinal; color between RHS N163C and RHS 169C.

*Pollen*.—Abundant; color nearest RHS 13C.

Gynoecium: One, two-beaked; half-inferior; 9.0 mm long;

*Style*.—Bifid; exserted; split apart at apex of ovary; about 5.0 mm long and about 0.5 mm diameter; color nearest RHS NN155C.

*Stigma*.—Acute apex, about 0.5 mm diameter; color nearest RHS 155A.

*Ovary*.—Half-inferior, about 3.0 mm long and 2.0 mm diameter; ellipsoidal to globose; apex acute, base rounded; color nearest RHS 145C.

Fruit: Two-beaked ellipsoidal capsule; about 4.5 mm long and 3.0 mm across; color nearest RHS 200B;

Seed: Thin ellipsoidal; less than 1.0 mm long and less than 0.5 mm wide; color between RHS 202A and RHS 200A;

Growth: 'Toffee Tart' grows best with ample moisture and drainage in either sun or shade. Cold hardy from USDA zones 4 to 9.

Disease and pest tolerance: Resistance and tolerance outside of that normal for *Heuchera* is not known.

It is claimed:

1. The new and distinct *Heuchera* plant named 'Toffee Tart' as herein described and illustrated.

* * * * *